United States Patent [19]

Krapcho

[11] Patent Number: 4,468,519

[45] Date of Patent: Aug. 28, 1984

[54] ESTERS OF PHOSPHINYLALKANOYL SUBSTITUTED PROLINES

[75] Inventor: John Krapcho, Somerset, N.J.

[73] Assignee: E. R. Squibb & Sons, Inc., Princeton, N.J.

[21] Appl. No.: 388,371

[22] Filed: Jun. 14, 1982

[51] Int. Cl.³ .................. C07F 9/65; A61K 31/675
[52] U.S. Cl. ............................. 548/409; 548/413; 424/200
[58] Field of Search ................. 548/409, 413, 414; 424/200

[56] References Cited

U.S. PATENT DOCUMENTS

| | | | |
|---|---|---|---|
| 4,105,776 | 8/1978 | Ondetti et al. | 424/274 |
| 4,168,267 | 9/1979 | Petrillo, Jr. | 548/413 |
| 4,311,697 | 1/1982 | Krapcho | 424/240 |
| 4,316,905 | 2/1982 | Krapcho | 424/274 |
| 4,316,906 | 2/1982 | Ondetti et al. | 424/274 |
| 4,337,201 | 6/1982 | Petrillo, Jr. | 548/413 |
| 4,374,131 | 2/1983 | Petrillo, Jr. | 424/200 |
| 4,381,297 | 4/1983 | Karanewsky et al. | 424/200 |

Primary Examiner—Donald G. Daus
Assistant Examiner—Diana G. Rivers
Attorney, Agent, or Firm—Lawrence S. Levinson; Donald J. Barrack

[57] ABSTRACT

Hypotensive activity is exhibited by compounds having the formula

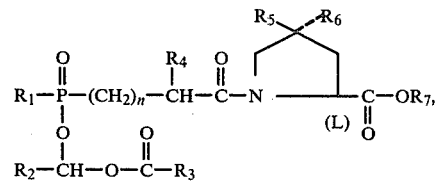

and salts thereof wherein $R_1$ is alkyl, aryl, arylalkyl, cycloalkyl, or cycloalkylalkyl;

$R_2$ is cycloalkyl, 3-cyclohexenyl or 2-alkyl-3-cyclohexenyl;

$R_3$ is alkyl, cycloalkyl, phenyl or alkoxy;

$R_4$ is hydrogen or alkyl;

one of $R_5$ and $R_6$ is hydrogen and the other is alkyl-X-, phenyl-X-, alkoxy, phenyloxy, phenyl, cycloalkyl, alkyl, or phenylalkyl; or together $R_5$ and $R_6$ are $-XCH_2CH_2X-$;

$R_7$ is hydrogen or

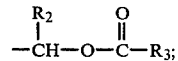

and
n is 0 or 1.

9 Claims, No Drawings

ESTERS OF PHOSPHINYLALKANOYL SUBSTITUTED PROLINES

RELATED APPLICATIONS

U.S. patent application Ser. Nos. 212,911, filed Dec. 4, 1980, now U.S. Pat. No. 4,337,201, issued June 29, 1982 and 326,082, filed Nov. 30, 1981, now U.S. Pat. No. 4,384,123, issued May 17, 1983, disclose inter alia, angiotensin-converting enzyme inhibitors having the formula

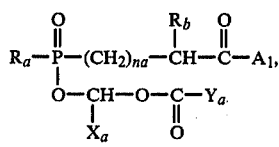

wherein $R_a$ is alkyl, aryl, arylalkyl, cycloalkyl or cycloalkylalkyl; $X_a$ is hydrogen, alkyl, or phenyl and $Y_a$ is hydrogen, alkyl, phenyl or alkoxy, or together $X_a$ and $Y_a$ are $-(CH_2)_2-$, $-(CH_2)_3-$, $-CH=CH-$ or

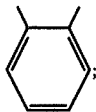

$R_b$ is hydrogen or alkyl and $A_1$ is certain specifically defined proline or substituted proline groups, and esters thereof.

BACKGROUND OF THE INVENTION

The recent literature discloses a variety of mercaptoacyl amino acids which are useful for inhibiting the conversion of angiotensin I to angiotensin II in mammals, and are, therefore, useful in the treatment of hypertension.

U.S. Pat. No. 4,105,776 discloses mercaptoacyl amino acids wherein the amino acid is, inter alia, proline, 4-hydroxyproline or 4-alkylproline.

U.S. Pat. No. 4,311,697 discloses mercaptoacyl amino acids wherein the amino acid is, inter alia, 1,4-dithia-7-azaspiro[4.4]nonane-8-carboxylic acid.

U.S. Pat. No. 4,316,905 discloses mercaptoacyl amino acids wherein the amino acid is, inter alia, 4-substituted proline and the 4-substituent is phenyl, cycloalkyl, or phenylalkyl.

U.S. Pat. No. 4,316,906 discloses mercaptoacyl amino acids wherein the amino acid is, inter alia, 4-substituted proline and the 4-substituent is alkylthio, phenylthio, alkoxy or phenyloxy.

The compounds disclosed by the above mentioned references are disclosed as inhibitors of the action of angiotensin converting enzyme in mammals and as useful hypotensive agents.

BRIEF DESCRIPTION OF THE INVENTION

Compounds having the formula

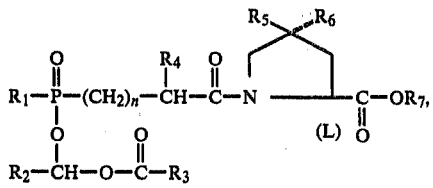

and salts thereof, have hypotensive activity. In formula I, and throughout the specification, the symbols are as defined below.

$R_1$ is alkyl, aryl, arylalkyl, cycloalkyl, or cycloalkylalkyl;

$R_2$ is cycloalkyl, 3-cyclohexenyl, or 2-alkyl-3-cyclohexenyl;

$R_3$ is alkyl, cycloalkyl or phenyl;

$R_4$ is hydrogen or alkyl;

one of $R_5$ and $R_6$ is hydrogen and the other is alkyl-X-, phenyl-X-, alkoxy, phenyloxy, phenyl, cycloalkyl, alkyl, or phenylalkyl; or together $R_5$ and $R_6$ are $-XCH_2CH_2X-$; and X is $-S-$,

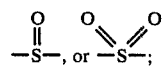

$R_7$ is hydrogen or

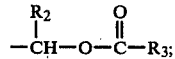

and n is 0 or 1.

The term "aryl", as used throughout the specification either by itself or as part of a larger group, refers to phenyl or phenyl substituted with halogen, alkyl, alkoxy, alkylthio, hydroxy, alkanoyl, nitro, amino, dialkylamino, or trifluoromethyl groups. Phenyl and monosubstituted phenyl are preferred and phenyl is the most preferred.

The term "alkyl", as used throughout the specification either by itself or as part of a large group, refers to groups having 1 to 10 carbon atoms. Alkyl groups having 1 to 4 carbon atoms are preferred.

The term "cycloalkyl", as used throughout the specification either by itself or as part of a larger group, refers to groups having 3 to 7 carbon atoms.

The term "alkoxy", as used throughout the specification either by itself or as part of a larger group, refers to groups having 1 to 8 carbon atoms. Alkoxy groups having 1 to 3 carbon atoms are preferred.

The term "halogen" or "halo", as used throughout the specification either by itself or as part of a larger group, refers to fluorine, chlorine, bromine and iodine. The preferred halogen groups are fluorine and chlorine.

The term "alkanoyl", as used throughout the specification either by itself or as part of a larger group, refers to groups having 2 to 9 carbon atoms.

DETAILED DESCRIPTION OF THE INVENTION

The compounds of formula I, and salts thereof, are hypotensive agents. They inhibit the conversion of the decapeptide angiotensin I to angiotensin II and, therefore, are useful in reducing or relieving angiotensin related hypertension. The action of the enzyme renin or angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→(ACE)-→angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two or four divided daily doses, provided on a basis of about 0.1 to 100 mg per kilogram of body weight per day, preferably about 1 to 15 mg per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg, preferably about 30 to 330 mg of a compound of this invention, and about 15 to 300 mg, preferably about 15 to 200 mg of the diuretic, to a mammalian species in need thereof. Exemplary of the diuretics contemplated for use in combination with a peptide of this invention are the thiazide diuretics, e.g., chlorthiazide, hydrochlorthiazide, flumethiazide, hydroflumethiazide, bendroflumethiazide, methychlothiazide, trichloromethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg of a compound of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of this invention can be prepared from the corresponding phosphinylalkanoyl proline derivatives having the formula

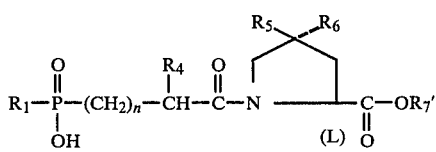

and an activated form of a carboxylic acid ester having the formula

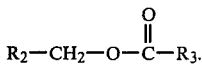

In formula II, and throughout the specification, $R_7'$ is

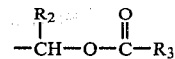

or a carboxylic acid protecting group, such as benzhydryl, t-butoxy, benzyl, and others well known in the art. Reaction of a compound of formula II and an activated form of a carboxylic acid ester of formula III yields the corresponding compound having the formula

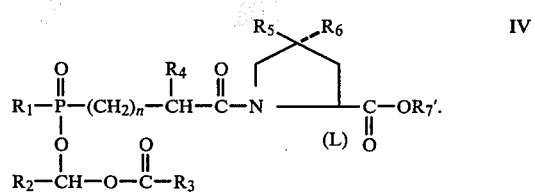

The reaction proceeds most readily in a polar organic solvent, such as dimethylformamide, in the presence of an organic base such as triethylamine.

To prepare the products of formula I wherein $R_7$ is hydrogen, the corresponding compound of formula IV (wherein $R_7'$ is a carboxylic acid protecting group) is deprotected. The particular deprotection reaction used will, of course, depend on the particular $R_7'$ group. If, for example, $R_7'$ is benzhydryl, deprotection can be accomplished by treating the protected compound with trifluoroacetic acid and anisole.

The starting phosphinylalkanoyl proline derivatives of formula II can be prepared utilizing the procedures described in United States patent application Ser. No. 212,911, filed Dec. 4, 1980, now U.S. Pat. No. 4,337,201, issued June 29, 1982. The procedure described therein comprises reacting a proline derivative having the formula

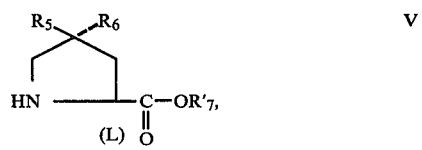

with a phosphinyl-acetic or propionic acid having the formula

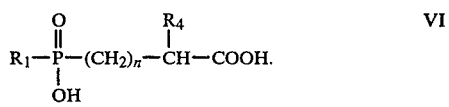

The reaction can be accomplished using known amide bond forming procedures. For example, the reaction can be run in the presence of a coupling agent such as dicyclohexylcarbodiimide, or the acid of formula VI can be activated by formation of its mixed anhydride, symmetrical anhydride, acid halide (preferably acid chloride) or acid ester, or by the use of Woodward reagent K, N-ethoxycarbonyl-2-ethoxy-1,2-dihydroquinoline, N,N'-carbonyldiimidazole or the like. A review of these methods can be found in *Methoden der Organischen Chemie* (Houben-Weyl), Vol. XV, part II, page 1 et seq. (1974).

The starting carboxylic acid ester will preferably be utilized in an activated form. One such form has the formula

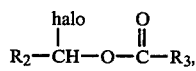
                                    VII wherein the chlorine is the preferred "halo" atom. A compound of formula VII can be prepared by reacting an aldehyde having the formula

                                    VIII with an acyl halide (preferably an acyl chloride) having the formula

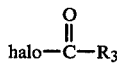
                                    IX in the presence of zinc chloride, preferably in an inert solvent such as dichloromethane.

Preferably, the compounds of this invention which contain a sulfone or sulfoxide group in the 4-position of the proline ring are prepared by oxidation of the corresponding thio compound. Use of the proper amount of an oxidizing agent such as m-chloroperbenzoic acid yields the desired sulfone or sulfoxide.

An alternative preparation for the compounds of this invention utilizes a protected derivative of a phosphinyl-acetic or propionic acid of formula VI and an activated form of a carboxylic acid ester of formula III as starting materials. Reaction of the starting materials in the presence of an organic base yields the corresponding compound having the formula

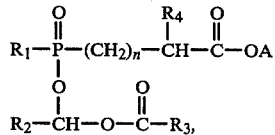
                                    X wherein A is a carbonyl protecting group. Deprotection of a compound of formula X can be accomplished using conventional techniques, the choice of which will depend on the protecting group used, and yields a compound having the formula

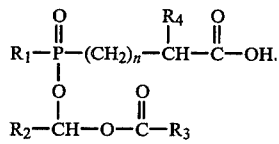
                                    XI

A compound of formula XI can be reacted with a proline derivative having the formula

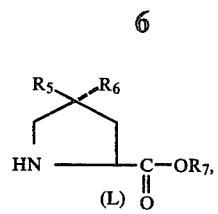
                                                XII using known amide bond forming procedures which have been referenced above, to yield the corresponding product of formula I.

The compounds of formula I wherein $R_7$ is hydrogen, form basic salts with various inorganic and organic bases which are also within the scope of the invention. Such salts include ammonium salts, alkali metal salts like lithium, sodium and potassium salts (which are preferred), alkaline earth metal salts like the calcium and magnesium salts, salts with organic bases, e.g., dicyclohexylamine salt, benzathine, diisopropyl amine, N-methyl-D-glucamine, hydrabamine salts, salts with amino acids like arginine, lysine and the like. The nontoxic, physiologically acceptable salts are preferred, although other salts are also useful, e.g., in isolating or purifying the product. The salts are formed using conventional techniques.

The following examples are specific embodiments of this invention.

EXAMPLE 1

(S)-7-[[[Cyclohexyl(1-oxopropoxy)methoxy](4-phenylbutyl)phosphinyl]acetyl]-1,4-dithia-7-azaspiro[4.4]nonane-8-carboxylic acid, lithium salt (A) (Chloro)cyclohexylmethyl propionate A stirred solution of 73 ml (0.84 mole) of propionyl chloride in 250 ml of dichloromethane was cooled to 0° C. (salt-ice bath) and treated portionwise with 94.2 g (0.84 mole) of freshly distilled cyclohexanecarboxaldehyde. After further cooling to −5° C., approximately 0.5 g of zinc chloride was added. The temperature rose gradually to 7° C. as a solid separated. The cooling bath was removed and while stirring was continued the reaction mixture was allowed to warm to room temperature (the solid gradually went into solution). After about 1 hour some additional zinc chloride was added; there was no further reaction. The solution was kept overnight at room temperature.

The mixture (darkened to a red-brown) was placed on a rotary evaporator to remove the bulk of solvent. The residual oil was taken up in 850 ml of ether, washed twice with 250 ml portions of ice-water (the color lightened to a pale yellow), then with 250 ml of saturated sodium chloride solution, dried (MgSO$_4$) and the solvent evaporated to give 166.5 g of an oil. The oil was distilled through a short glass helices-packed column and material boiling at 68°–75° C. (1 mm of Hg) was fractionated through the same column to yield 140.5 g of product; boiling point 67°–69° C. (1 mm of Hg). Anal. Calc'd for $C_{10}H_{17}ClO_2$: Cl, 17.32% Found: Cl, 17.20%

(B)

(S)-7-[[[Cyclohexyl(1-oxopropoxy)methoxy](4-phenylbutyl)phosphinyl]acetyl]-1,4-dithia-7-azaspiro[4.4]nonane-8-carboxylic acid, benzhydryl ester A stirred suspension of 1.7 g (2.8 mmol) of N-[hydroxy(4-phenylbutyl)phosphinylacetyl]-4,4-ethylenedithio-L-proline, benzhydryl ester in 10 ml of dimethylformamide was cooled and treated with 0.56 g of (5.6 mmol) of triethylamine. To the resulting solution was added 2.2 g (10 mmol) of (chloro)cyclohexylmethyl propionate. After stirring for 3 hours at room temperature only a small amount of product was present. The mixture was then heated to 55° C. and heated and stirred overnight. After 19 hours, the mixture was cooled and treated with an additional 0.6 g of triethylamine and 2.2 g of (chloro)cyclohexylmethyl propionate and maintained at 55° C. for an additional 24 hours. The reaction mixture was diluted with 100 ml of ethyl acetate and 20 ml of water. The mixture was shaken and the aqueous phase was extracted with 25 ml of ethyl acetate. The organic phases were combined, extracted with 20 ml of water (two times), 20 ml of saturated sodium chloride solution, dried (MgSO$_4$) and filtered. The filtrate was evaporated to give 5.1 g of material. The material was purified by chromatography on 100 g of silica gel, (60–200 mesh, d=0.37 g/ml) using 2:1 ethyl acetate-hexane to give 1.0 g of foamy solid.

(C)
(S)-7-[[[Cyclohexyl(1-oxopropoxy)methoxy](4-phenylbutyl)phosphinyl]acetyl]-1,4-dithia-7-azaspiro[4.4]nonane-8-carboxylic acid A solution of 1.0 g (1.3 mmol) of (S)-7-[[[cyclohexyl(1-oxopropoxy)methoxy](4-phenylbutyl)phosphinyl]acetyl]-1,4-dithia-7-azaspiro[4.4]nonane-8-carboxylic acid, benzhydryl ester in 10 ml of dichloromethane was stirred, cooled in an ice-bath, treated with 0.3 ml of anisole and 1.0 ml of trifluoroacetic acid (dropwise). After 90 minutes, the solvent and bulk of excess of trifluoroacetic acid were removed on a rotary evaporator and the residue was shaken with 50 ml of ethyl acetate and 20 ml of cold water. The layers were separated (5 ml of ether was added to break up the emulsion) and the organic phase was washed with three 20 ml portions of water. After back-extracting the combined aqueous layers with 25 ml of ethyl acetate, the combined organic layers were washed with 20 ml of saturated sodium chloride, dried (MgSO$_4$), and the solvent evaporated to yield 1.26 g of a syrup. The syrup was purified by chromatography on 60 g of silica gel (60–200 mesh, d=0.37 g/ml) using 40:1:1 dichloromethane:methanol:acetic acid to give 0.74 g of a foam-like solid.

(D)
(S)-7-[[[Cyclohexyl(1-oxopropoxy)methoxy](4-phenylbutyl)phosphinyl]acetyl]-1,4-dithia-7-azaspiro[4.4]nonane-8-carboxylic acid, lithium salt A solution of 0.64 g (1.0 mmol) of (S)-7-[[[cyclohexyl(1-oxopropoxy)methoxy](4-phenylbutyl)phosphinyl]acetyl]-1,4-dithia-7-azaspiro[4.4]nonane-8-carboxylic acid in 17 ml of acetone was diluted with 4 ml of water and treated with 5.0 ml of 0.1M lithium carbonate (1 equivalent). The bulk of the acetone was removed on a rotary evaporator and the residue was diluted with 50 ml of water; a trace of suspended material was removed by a Millipore filtration. The filtrate was lyophilized to give 0.62 g of solid, melting point 90°–95° C.; $[\alpha]_D^{rt}$ −18.0° (c, 1%, methanol).

Anal. Calc'd for $C_{29}H_{41}NO_7PS_2 \cdot Li \cdot 1.5H_2O$: C, 54.02; H, 6.88; N, 2.17; P, 4.81; S, 9.95; Found: C, 54.14; H, 6.44; N, 2.32; P, 4.7; S, 9.83

EXAMPLE 2
(S)-7-[[[Cyclohexyl(1-oxopropoxy)methoxy](4-phenylbutyl)phosphinyl]acetyl]-1,4-dithia-7-azaspiro[4.4]nonane-8-carboxylic acid, sodium salt (A) [(Hydroxy)(4-phenylbutyl)phosphinyl]acetic acid, benzyl ester A stirred solution of 28 g (0.081 mole) of hydroxy(4-phenylbutyl)phosphinylacetic acid, benzyl ester in 200 ml of chloroform was cooled in ice-water, treated with 17 ml (0.122 mole) of triethylamine, followed by 25 g (0.122 mole) of chlorocyclohexylmethyl propionate and 5.5 g (0.15 mole) of tetrabutylammonium iodide, and the nearly colorless solution heated to gentle reflux for 22 hours. At the end of this period TLC (2:1 ethyl acetate-hexane and 4:1 tolueneacetic acid) of the still basic solution showed a small amount of starting material still present.

The bulk of chloroform was removed on a rotary evaporator and the oily residue (81 g) was taken up in 500 ml of ethyl acetate, washed with three 100 ml portions of ice-cold water, dried (MgSO$_4$), and the solvent evaporated to give 45.9 g of an oil. A portion of the oil (10 g) was chromatographed on 250 g of silica gel (density 0.4 g/ml; eluting with ethyl acetate-hexane, 1:1) to yield 6.0 g of a colorless oil.

TLC: R$_f$0.26 (1:1 ethyl acetate-hexane).

(B)
[[Cyclohexyl(1-oxopropoxy)methoxy](4-phenylbutyl)phosphinyl]acetic acid, benzyl ester A mixture of [(hydroxy)(4-phenylbutyl)phosphinyl]acetic acid, benzyl ester (4.4 g, 0.0085 mole), palladium (10%) on carbon catalyst (0.5 g) in ethyl acetate (40 ml) was shaken in a Parr reduction apparatus until the bottle gauge registered no further absorption of hydrogen. TLC, silica gel, dichloromethane/methanol/acetic acid (20:1:1) showed a single (elongated) spot centered at R$_f$ 0.56. The mixture was filtered through Celite. After concentration in vacuo, the product was obtained as an oil (3.6 g).

(C)
(S)-7-[[[Cyclohexyl(1-oxopropoxy)methoxy](4-phenylbutyl)phosphinyl]acetyl]-1,4-dithia-7-azaspiro[4.4]nonane-8-carboxylic acid A solution of [[cyclohexyl(1-oxopropoxy)methoxy](4-phenylbutyl)phosphinyl]acetic acid, benzyl ester (3.2 g, 0.0075 mole) in tetrahydrofuran (50 ml) was cooled in an ice-water bath and 1,1-carbonyldiimidazole (1.2 g, 0.0075 mole) was added. After one hour in the cold, 1,4-dithia-7-azaspiro[4.4]nonane-8-carboxylic acid.HCl (1.8 g, 0.0075 mole) was added, followed by triethylamine (1.5 g, 0.015 mole). The mixture was stirred at ambient temperature for 20 hours. After filtration, and concentration in vacuo, ethyl acetate (100 ml) was added to the residue. The mixture was washed with water, followed by 5% potassium acid sulfate to a pH of 1–2, brine, dried (MgSO$_4$) and concentrated in vacuo to give the recovery of a semi-solid (3.4 g). TLC, silica gel, toluene/acetic acid (4:1) showed a major (elongated) spot at R$_f$0.4 plus several minor spots at lower R$_f$values and one at a higher R$_f$value. After chromatography on silica gel (130 g), eluting with toluene/methanol (10:1) to give a recovery of product of inferior quality (2.8 g, showing 4 contaminants), it was rechromatographed on silica gel (110 g), eluting with toluene/methanol/acetic acid (40:1:1) to give a recovery of 1.9 g. TLC, silica gel, toluene/acetic acid (4:1) showed a single (elongated) spot, $R_f 0.40$.

(D)
(S)-7-[[[Cyclohexyl(1-oxopropoxy)methoxy](4-phenylbutyl)phosphinyl]acetyl]-1,4-dithia-7-azaspiro[4.4]nonane-8-carboxylic acid, sodium salt A 0.03M sodium bicarbonate solution was added portionwise to (S)-7-[[[cyclohexyl(1-oxopropoxy)methoxy](4-phenylbutyl)phosphinyl]acetyl]-1,4-dithia-7-azaspiro[4.4]nonane-8-carboxylic acid (1.6 g, 0.0025 mole) to a pH of 6.2 (ca. 70 ml, 0.023 mole) with stirring. The pH was monitored by a pH meter, and argon was bubbled through the mixture to remove carbon dioxide as it was formed. After the addition of one half an equivalent (ca. 40 ml), acetone was added (10 ml) to facilitate dissolution of the starting material; at this point the separation of a granular solid was observed. (The solid remained insoluble at a pH of 6.2; after the removal of the acetone by concentration in vacuo, the solid was recovered by filtration (130 mg, 0.002 mole)). It was recrystallized from acetonitrile (100 mg/5 ml) with a recovery of 50 mg, melting point 150°–151.5° C. The aqueous filtrate (pH 6.3) was Millipore filtered and lyophilized to give the title compound as a hygroscopic solid (1.4 g).

Anal. Calc'd for $C_{29}H_{41}H_{41}NO_7PS_2 \cdot 0.75H_2O$: Calc'd: C, 53.81; H, 6.62; N, 2.16; P, 4.79; S, 9.91; Found: C, 53.78; H, 6.53; N, 1.96; P, 4.8; S, 9.77

The following is a list of additional compounds which are exemplary of the invention disclosed herein.

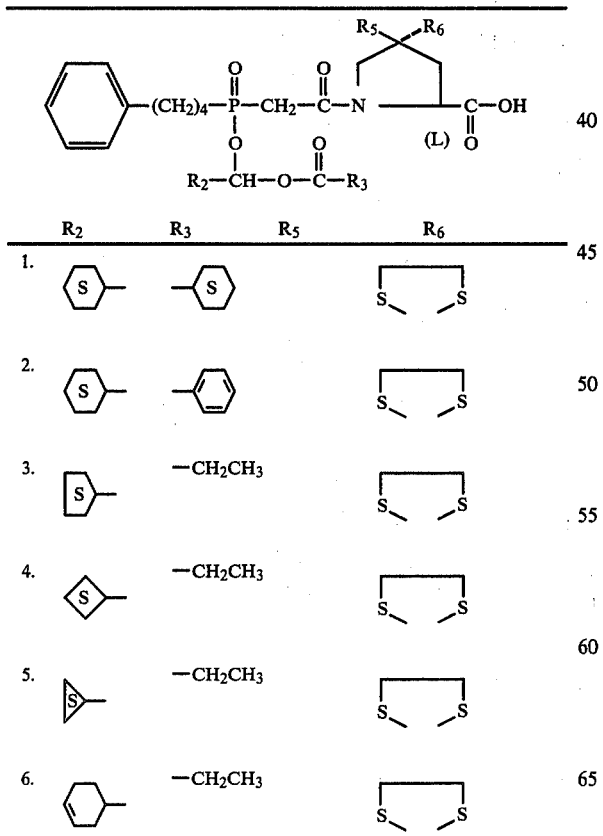

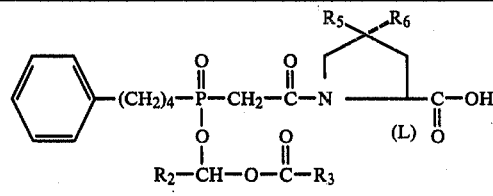

| | $R_2$ | $R_3$ | $R_5$ | $R_6$ |
|---|---|---|---|---|
| 7. | 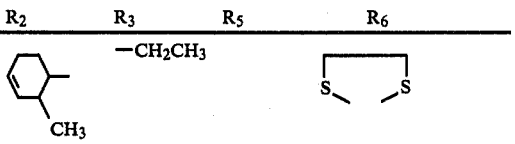 cyclohexenyl-CH₃ | —CH₂CH₃ | | S—S ring |
| 8. | thiophene | —CH₂CH₃ | —S—CH₂CH₃ | H |
| 9. | thiophene | —CH₂CH₃ | H | —S—CH₂CH₃ |
| 10. | thiophene | —CH₂CH₃ | —S—phenyl | H |
| 11. | thiophene | —CH₂CH₃ | H | —S—phenyl |
| 12. | thiophene | —CH₂CH₃ | —CH₂—phenyl | H |
| 13. | thiophene | —CH₂CH₃ | H | —CH₂—phenyl |
| 14. | thiophene | —CH₂CH₃ | phenyl | H |
| 15. | thiophene | —CH₂CH₃ | H | phenyl |
| 16. | thiophene | —CH₂CH₃ | thiophene | H |
| 17. | thiophene | —CH₂CH₃ | H | thiophene |

What is claimed is:
1. A compound having the formula

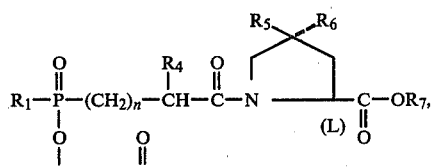

or a salt thereof, wherein
$R_1$ is alkyl, aryl, arylalkyl, cycloalkyl, or cycloalkylalkyl;
$R_2$ is cycloalkyl, 3-cyclohexenyl, or 2-alkyl-3-cyclohexenyl;
$R_3$ is alkyl, cycloalkyl, phenyl or alkoxy;
$R_4$ is hydrogen or alkyl;

one of $R_5$ and $R_6$ is hydrogen and the other is alkyl-X-, phenyl-X-, alkoxy, phenyloxy, phenyl, cycloalkyl, alkyl, or phenylalkyl; or together $R_5$ and $R_6$ are $-XCH_2CH_2X-$; and X is $-S-$,

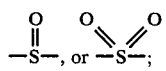

$R_7$ is hydrogen or

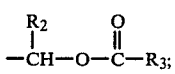

and n is 0 or 1.

2. A compound in accordance with claim 1 wherein $R_2$ is cycloalkyl.

3. A compound in accordance with claim 1 wherein $R_2$ is 3-cyclohexenyl or 2-alkyl-3-cyclohexenyl.

4. A compound in accordance with claim 2 wherein $R_1$ is 4-phenylbutyl.

5. A compound in accordance with claim 2 wherein $R_4$ is hydrogen.

6. A compound in accordance with claim 2 wherein $R_7$ is hydrogen.

7. A compound in accordance with claim 2 wherein n is 0.

8. A compound in accordance with claim 1 wherein $R_1$ is 4-phenylbutyl, $R_2$ is cyclohexyl, $R_4$ is hydrogen, $R_7$ is hydrogen and n is 0.

9. The compound in accordance with claim 1, (S)-7-[[[cyclohexyl(1-oxopropoxy)methoxy](4-phenylbutyl)phosphinyl]acetyl]-1,4-dithia-7-azaspiro[4.4]nonane-8-carboxylic acid, or a salt thereof.

* * * * *